United States Patent
Boday et al.

(10) Patent No.: US 10,167,367 B2
(45) Date of Patent: Jan. 1, 2019

(54) POLYCARBONATE BASED PI-PI STABILIZED NANO-OBJECTS AND HYDROGELS

(71) Applicant: International Business Machines Corporation, Armonk, NY (US)

(72) Inventors: Dylan J. Boday, Tucson, AZ (US); Mareva B. Fevre, San Jose, CA (US); Jeannette M. Garcia, San Leandro, CA (US); James L. Hedrick, Pleasanton, CA (US); Nathaniel H. Park, San Jose, CA (US); Rudy J. Wojtecki, San Jose, CA (US); Mu San Zhang, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 43 days.

(21) Appl. No.: 15/332,010

(22) Filed: Oct. 24, 2016

(65) Prior Publication Data
US 2018/0112041 A1    Apr. 26, 2018

(51) Int. Cl.
| C08G 64/18 | (2006.01) |
| C08G 81/00 | (2006.01) |
| C08L 87/00 | (2006.01) |
| C08G 64/16 | (2006.01) |
| A61K 47/34 | (2017.01) |

(52) U.S. Cl.
CPC ......... *C08G 81/00* (2013.01); *C08G 64/1633* (2013.01); *C08G 64/183* (2013.01); *C08L 87/005* (2013.01); *A61K 47/34* (2013.01); *C08G 64/18* (2013.01); *C08G 2210/00* (2013.01); *C08L 2205/025* (2013.01)

(58) Field of Classification Search
None
See application file for complete search history.

(56) References Cited

U.S. PATENT DOCUMENTS

| 6,437,040 B2 | 8/2002 | Anthony et al. |
| 6,506,837 B2 | 1/2003 | Destarac et al. |
| 8,470,891 B2 | 6/2013 | Hedrick et al. |
| 8,728,528 B2 | 5/2014 | Biggs et al. |
| 9,216,529 B2 | 12/2015 | Swinnen et al. |
| 2003/0027871 A1 | 2/2003 | Bendejacq et al. |
| 2010/0305281 A1* | 12/2010 | Fujiwara ............... C07D 319/06 525/461 |
| 2014/0058058 A1 | 2/2014 | Song et al. |
| 2014/0155549 A1 | 6/2014 | Swinnen et al. |

FOREIGN PATENT DOCUMENTS

| GB | 965085 A | 7/1964 |
| WO | WO-01/16187 A1 | 3/2001 |

OTHER PUBLICATIONS

Chan; Tetra-n-butylammonium Flouride as an Efficient Tranesterification Catalyst for Functioning Cyclic Carbonates and Aliphatic Polycarbonates; ACS Macro Letters (2013) 2 pp. 860-864. (Year: 2013).*

* cited by examiner

*Primary Examiner* — David J Buttner
(74) *Attorney, Agent, or Firm* — Roy R. Salvagio; Kelsey M. Skodje; Kennedy Lenart Spraggins LLP

(57) ABSTRACT

A block copolymer includes a water-soluble block that is bonded to one or more hydrophobic polycarbonate blocks that include pendant fluoroaryl substituents.

2 Claims, 10 Drawing Sheets

POLYCARBONATE BASED PI-PI STABILIZED NANO-OBJECTS AND HYDROGELS

BACKGROUND

Molecules that include arene groups associate through supramolecular interactions to produce aggregates by arene stacking (also referred to as pi-pi stacking). One example of an arene stacking configuration includes stacking whereby two parallel arenes associate off-centered in a "slipped" stacking configuration. Another example of an arene stacking configuration includes perpendicular arenes that associate in an "edge-on" stacking configuration. Yet another example of an arene stacking configuration is a configuration in which perfluoroarenes with electron-rich arenes are oriented in a parallel-displaced or "face-to-face" configuration, representing the most stable configuration.

The interaction between single arene molecules is generally a weak supramolecular interaction (e.g., having ΔG of about −1 to −2 kcal per mole). However, these weak supramolecular interactions are generally considered additive. Accordingly, while the interaction is weak between small molecules, the interaction can be orders of magnitude stronger when these functionalities are present in repeat units of a polymer.

SUMMARY

According to an embodiment, a block copolymer is disclosed. The block copolymer includes a water-soluble block that is bonded to one or more hydrophobic polycarbonate blocks that include pendant fluoroaryl substituents.

According to another embodiment, a mixture of block copolymers is disclosed. The mixture includes a water-soluble block bonded to one or more hydrophobic polycarbonate blocks. The one or more hydrophobic polycarbonate blocks include pendant fluoroaryl substituents, pendant aryl substituents, or a combination thereof.

According to another embodiment, a method of forming a material that is stabilized by fluoroarene-arene pi-pi stacking is disclosed. The material may include a nano-object in aqueous media that is stabilized by the fluoroarene-arene pi-pi stacking or a shear-thinning physical hydrogel that is stabilized by the fluoroarene-arene pi-pi stacking.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

Figure 1:
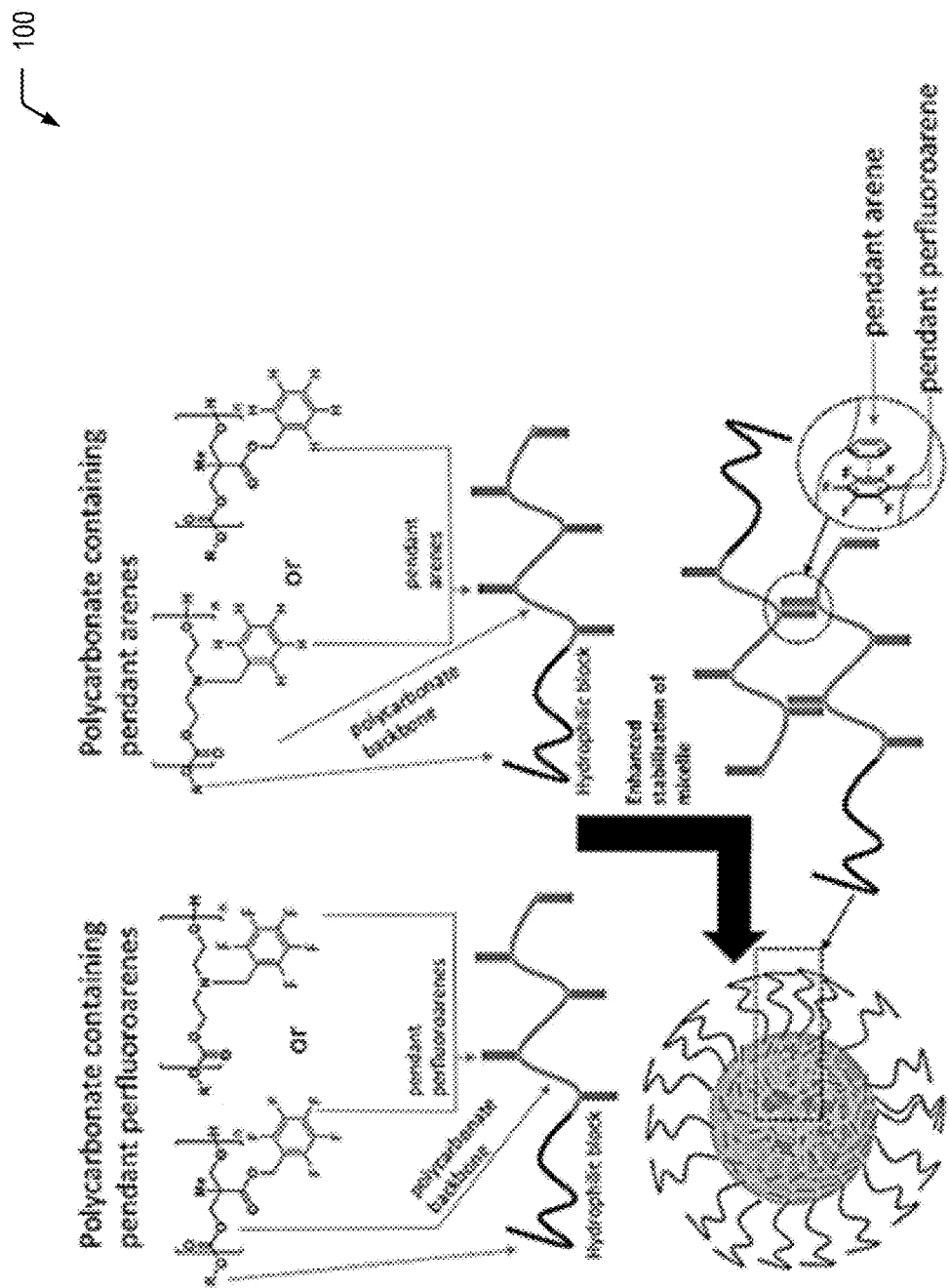
FIG. 1 is a diagram illustrating a method to enhance micelle stability from the combination of a polycarbonate block copolymer containing pendant arene and perfluoroarene substituents, according to one embodiment.

The present disclosure describes a macromolecular composition of PEG and polycarbonate block copolymers containing pendant fluoroaryl and/or aryl substituents and self-assembly of these polymers or mixture of polymers into nanoscale objects or hydrogels. The pi-pi interactions between fluoroarene and arene moieties are more favorable and were shown to adopt different spatial arrangements as compared to arene-arene interactions. Therefore, the nano-objects or hydrogels obtained by self-assembly of the aforementioned polymers or mixtures of polymers may be more stable. Moreover, the composition of the copolymers may influence the nature/size of the nano-objects/hydrogels.

While the pi-pi stacking interactions between arene molecules have been used as a means to control self-assembly of nano-objects in solution, interactions between electron-poor perfluoroarenes and arenes remain poorly studied for that purpose. Perfluoroarenes associate favorably with electron-rich arene functionalities and can lead to more stable aggregates than simple arene-arene pi-pi stacking (e.g., a higher association constant or binding energy). As an example, the ΔE for interactions between a perfluoroarene group and an arene group has been shown to be on the order of −5 kcal per mole. Moreover, while a "slipped" configuration and a T-shaped configuration may be favored for arene-arene interactions, the "slipped" and "face-to-face" configurations are favored for arene-perfluoroarene interactions. Therefore, perfluoroarene-arene interactions have been utilized for orientation of crystals, topochemical/sequence-controlled polymerization of acetylene monomers or formation of organogels using small molecules.

While pi-pi arene interactions have been demonstrated for stabilization of micelles, fluoroarene-arene interactions have not been utilized for the stabilization of nano-objects in aqueous solution. The synthesis of more stable nano-objects (e.g., micelles, etc.) remains a challenge in areas such as drug delivery. Due to the potential toxicity of drugs (e.g., anti-cancer agents) or the development of more patient-friendly delivery methods, the formulation of drugs in encapsulating entities that are stable for extended periods (e.g., several months) may be valuable.

Fluoroarene-arene interactions have been utilized for the formation of β-hairpin mimics in solution by intramolecular folding of poly(styrene)-b-poly(n,n-dimethylacrylamide)-b-poly(pentafluorostyrene) triblock copolymers. Multi-compartment-micelles have been obtained with triblock copolymers bearing arene and pentafluoroarene hydrophobic blocks, resulting from the incompatibility of these hydrophobic blocks. However, polymers bearing fluoroarene substituents have not been utilized for nano-object stabilization. The present disclosure describes a composition for the synthesis of fluoroarene-substituted polycarbonate block copolymers and methods for the subsequent formulation of more stable nano-objects and polymer-based physical hydrogels.

Figure 4:
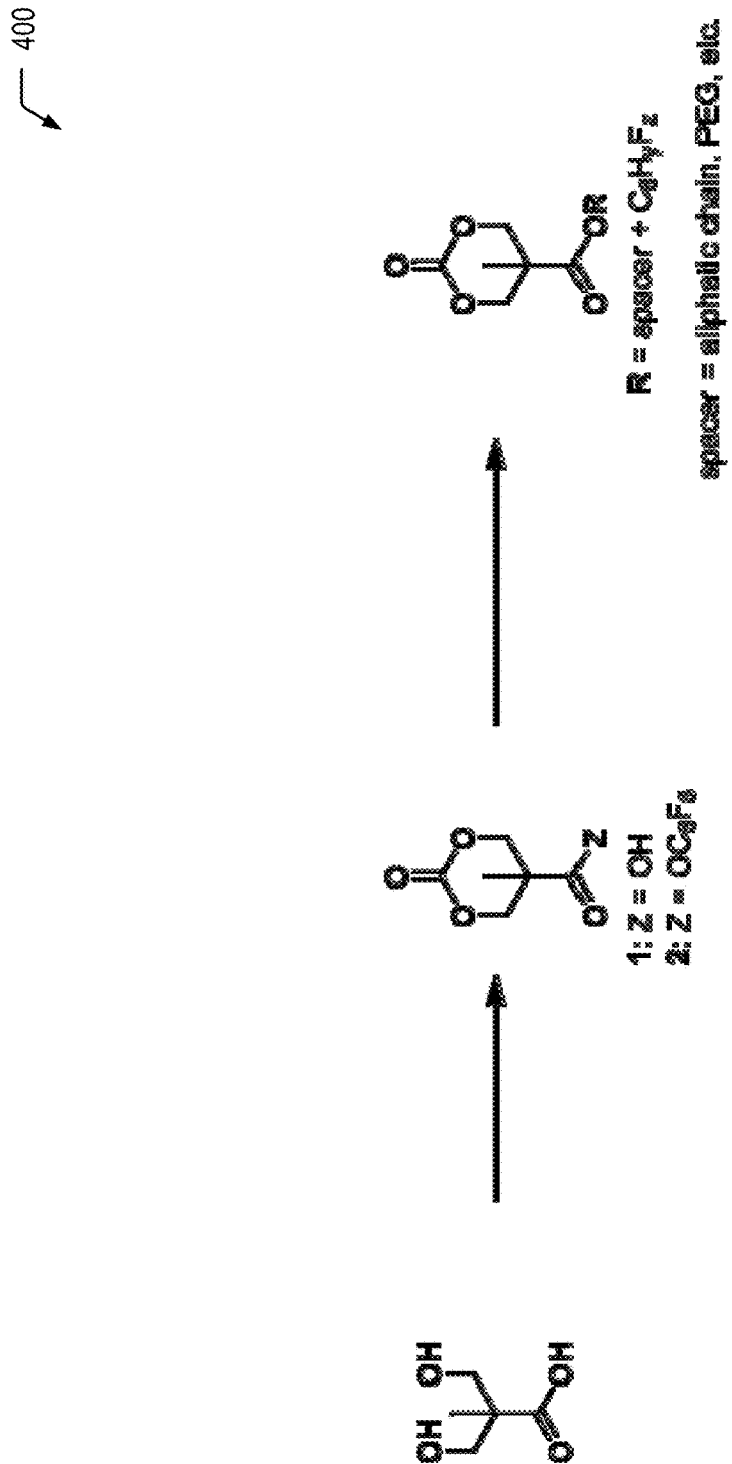
FIG. 4 is a chemical reaction diagram illustrating examples of synthetic routes to 6-membered cyclic carbonates with pendant fluorophenyl substituents.
Figure 5:
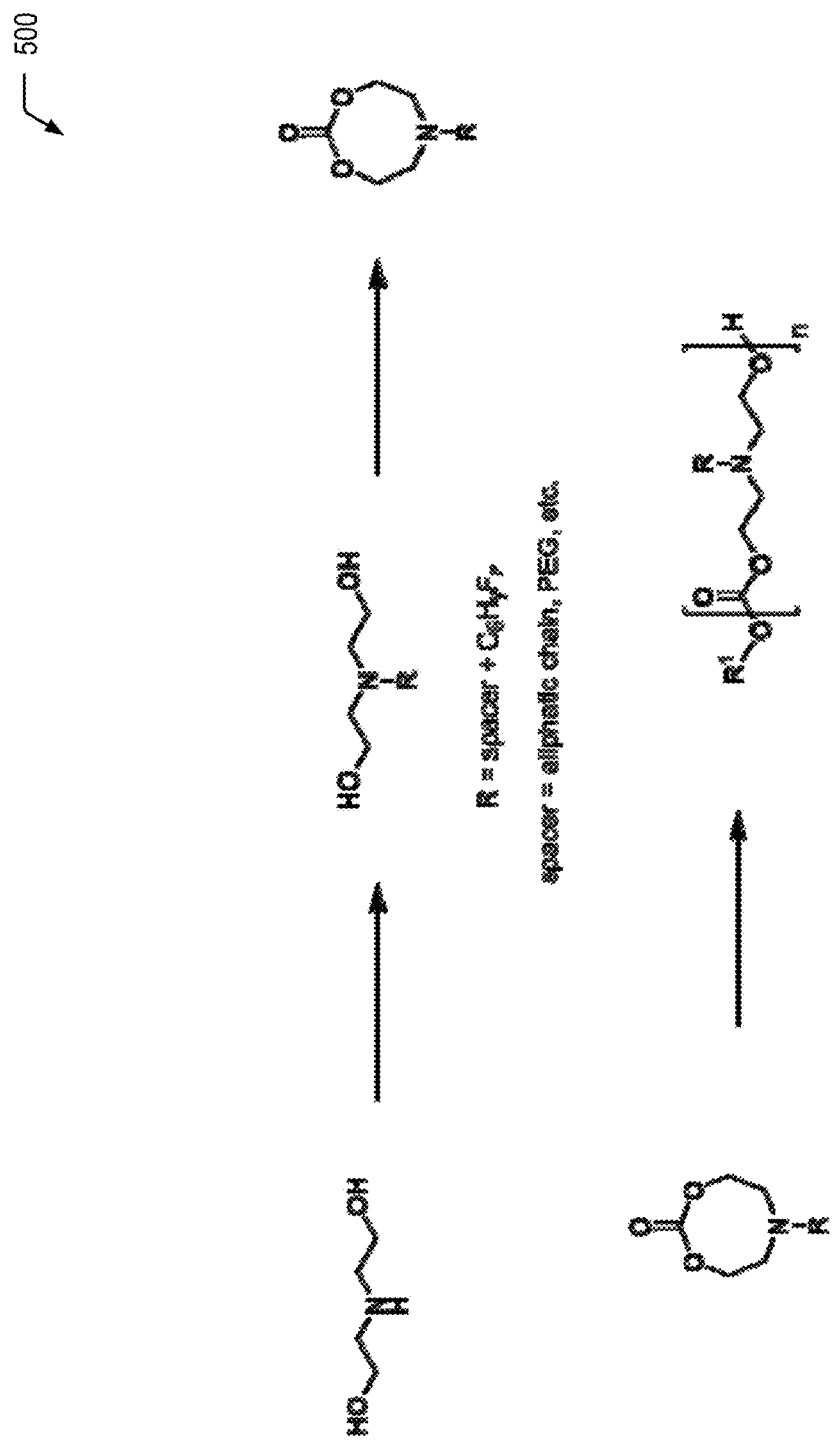
FIG. 5 is a chemical reaction diagram illustrating examples of synthetic routes to 8-membered cyclic carbonates with pendant fluorophenyl substituents.

In the present disclosure, fluorophenyl-substituted monomers may be obtained via techniques known to one of ordinary skill in the art (as depicted and further described herein with respect to FIGS. 4 and 5). Depending on the ability of the ester substituent (e.g., R, where R=spacer+ $C_6H_yF_z$) to be a good leaving group, the carbonate monomer may be polymerized by acid-catalyzed or base-catalyzed processes. For example, if R is a good leaving group, acid catalysis (e.g., triflic acid) may be used, as illustrated and further described herein with respect to FIG. 6. If R is not a good leaving group, base catalysis (e.g., DBU) may be used. For 6-membered monomers with pendant substituents attached with an amide or 8-membered monomers, base-catalyzed polymerization may be used, as illustrated and further described herein with respect to FIGS. 5 and 6. Depending on the alcohol initiator that is selected, homopolymers, amphiphilic diblock copolymers or triblock copolymers can be synthesized, as illustrated and further described herein with respect to FIGS. 7A-7B and FIGS. 8A-8B. Alternatively, the fluorophenyl-containing monomer may be copolymerized with one or several carbonate monomers bearing other substituents (e.g., statistical, multiblock, gradient copolymers).

Figure 2:
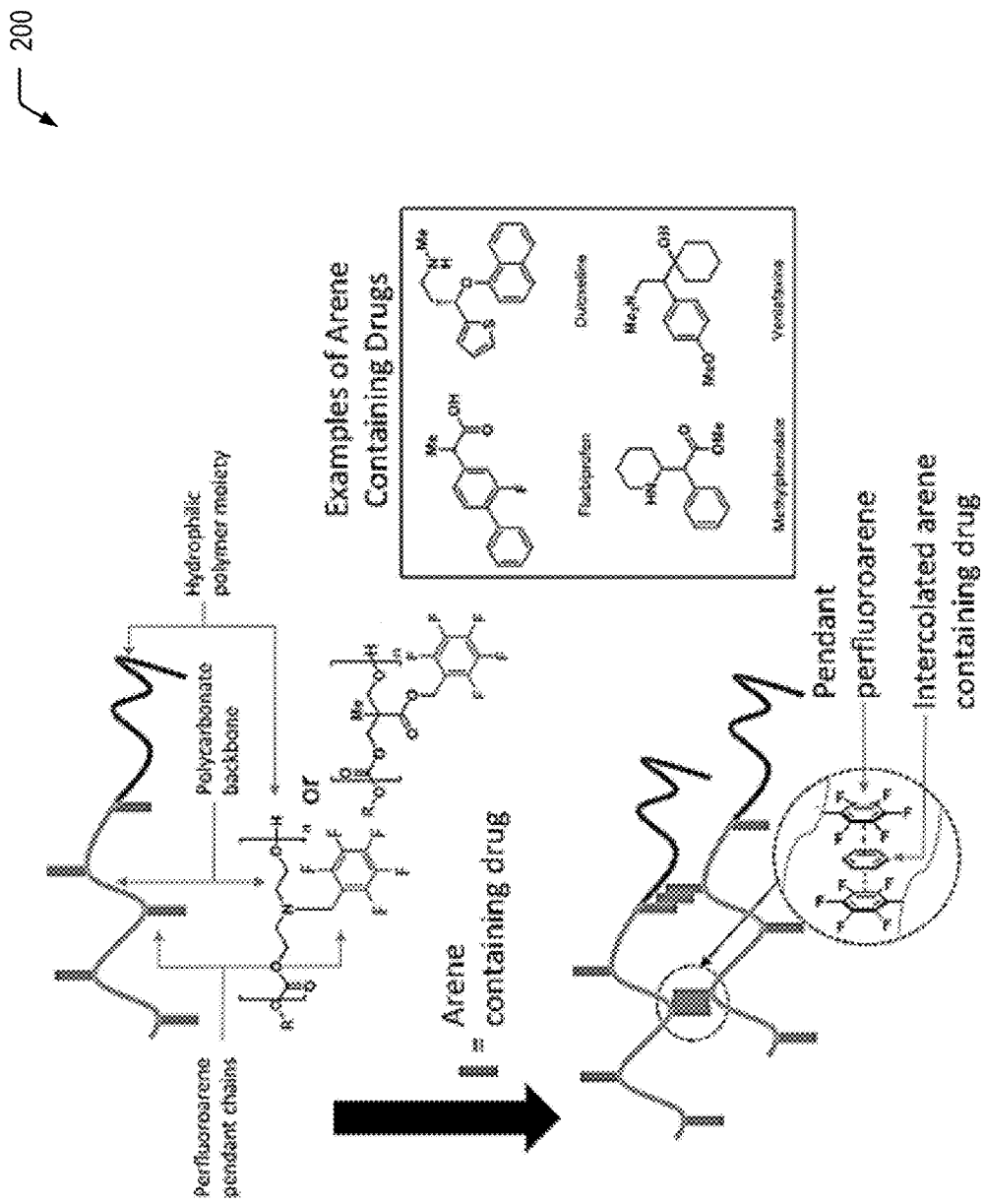
FIG. 2 is a diagram illustrating how pi-pi interactions work to encourage drug loading, according to one embodiment.
Figure 3:
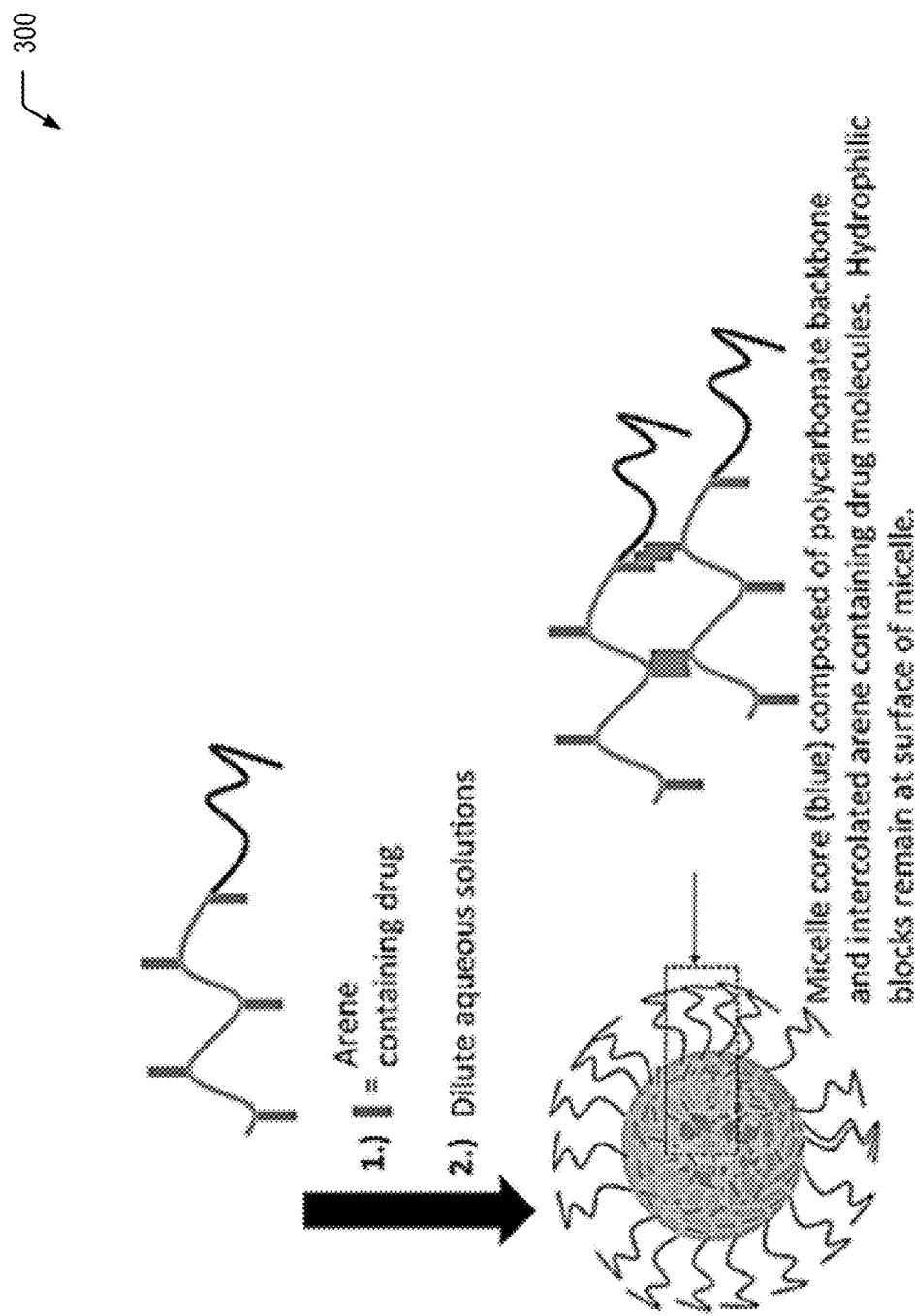
FIG. 3 is a diagram illustrating how arene stacking between pendant perfluoroarene and arene containing drugs further stabilize the micelle and enable high drug loading capacity, according to one embodiment.

Referring to FIG. 1, a diagram 100 depicts an illustrative, non-limiting example of a method of enhancing micelle stability from the combination of polycarbonate block copolymers containing pendant arene and perfluoroarene substituents. As described further herein, the same method and mechanism depicted in FIG. 1 may apply to the preparation of physical hydrogels from the appropriate triblock copolymers. In the context of drug loading, FIG. 2 a diagram 200 depicts an example of how pi-pi interactions encourage drug loading, and FIG. 3 a diagram 300 depicts an example of a micelle formed from a combination of the hydrophobic effect and arene stacking. Arene stacking between pendant perfluoroarene and arene containing drugs further stabilize the micelle and allow high drug-loading capacity.

Referring to FIG. 4, a chemical reaction diagram 400 illustrates examples of synthetic routes to 6-membered cyclic carbonates with pendant fluorophenyl substituents (z>0). In the first chemical reaction depicted on the left side of FIG. 4, known literature procedures may be utilized to form the intermediate material depicted on the right side of the first chemical reaction. In the second chemical reaction depicted on the right side of FIG. 4, in the case where Z=OH (designated as "1" in FIG. 4), oxalyl chloride, TEA, THF, then ROH may be utilized to form the 6-membered cyclic carbonate with pendant fluorophenyl substituents depicted on the right side of the second chemical reaction diagram. In the second chemical reaction depicted on the right side of FIG. 4, in the case where $Z=OC_6F_5$ (designated as "2" in FIG. 4), TBAF, ROH, and THF may be utilized to form the 6-membered cyclic carbonate with pendant fluorophenyl substituents depicted on the right side of the second chemical reaction diagram. As depicted in FIG. 4, the letter R is used to designate a spacer and $C_6H_yF_z$, where the spacer may be an aliphatic chain or PEG, among other alternatives.

Referring to FIG. 5, a chemical reaction diagram 500 depicts an example of a synthetic route to an 8-membered cyclic carbonate with pendant fluorophenyl substituents (z>0). FIG. 5 illustrates that, in cases where the ester substituent (R) is not a good leaving group, the carbonate monomer may be polymerized via a base-catalyzed process. In the first chemical reaction depicted at the top left of FIG. 5, RX (where X=Br, Cl), $K_2CO_3$, MeCN or DMF may be utilized to form the intermediate material. As shown in FIG. 5, the letter R is used to designate a spacer and $C_6H_yF_z$, where the spacer may be an aliphatic chain or PEG, among other alternatives. In the second chemical reaction depicted at the top right of FIG. 5, ethyl chloroformate, TEA, and THF may be utilized to form the 8-membered cyclic carbonate monomer with the pendant fluorophenyl substituents. The third chemical reaction depicted at the bottom of FIG. 5 illustrates a ring-opening polymerization reaction utilizing the 8-membered cyclic carbonate monomer with the pendant fluorophenyl substituents.

Figure 6:
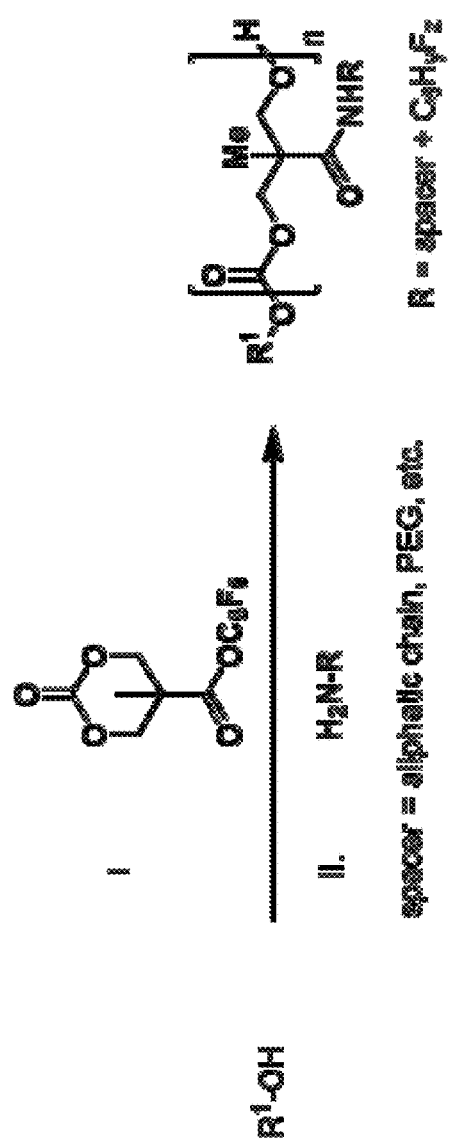
FIG. 6 is a chemical reaction diagram illustrating an example of a synthetic route to a polycarbonate with pendant amide fluorophenyl substituents.

Referring to FIG. 6, a chemical reaction diagram 600 depicts an example of a synthetic route to a polycarbonate with pendant amide fluorophenyl substituents (z>0). FIG. 6 illustrates that, in cases where the ester substituent (R) is a good leaving group, the carbonate monomer may be polymerized via an acid-catalyzed process. In FIG. 6, the chemical reaction includes an alcohol (designated "R'—OH" in FIG. 6), the intermediate material depicted in FIG. 4 (where $Z=OC_6F_5$), and an amine (designated as "$H_2N-R$" in FIG. 6) along with TEA and THF. As shown in FIG. 6, the letter R is used to designate a spacer and $C_6H_yF_z$, where the spacer may be an aliphatic chain or PEG, among other alternatives.

Figure 7A:
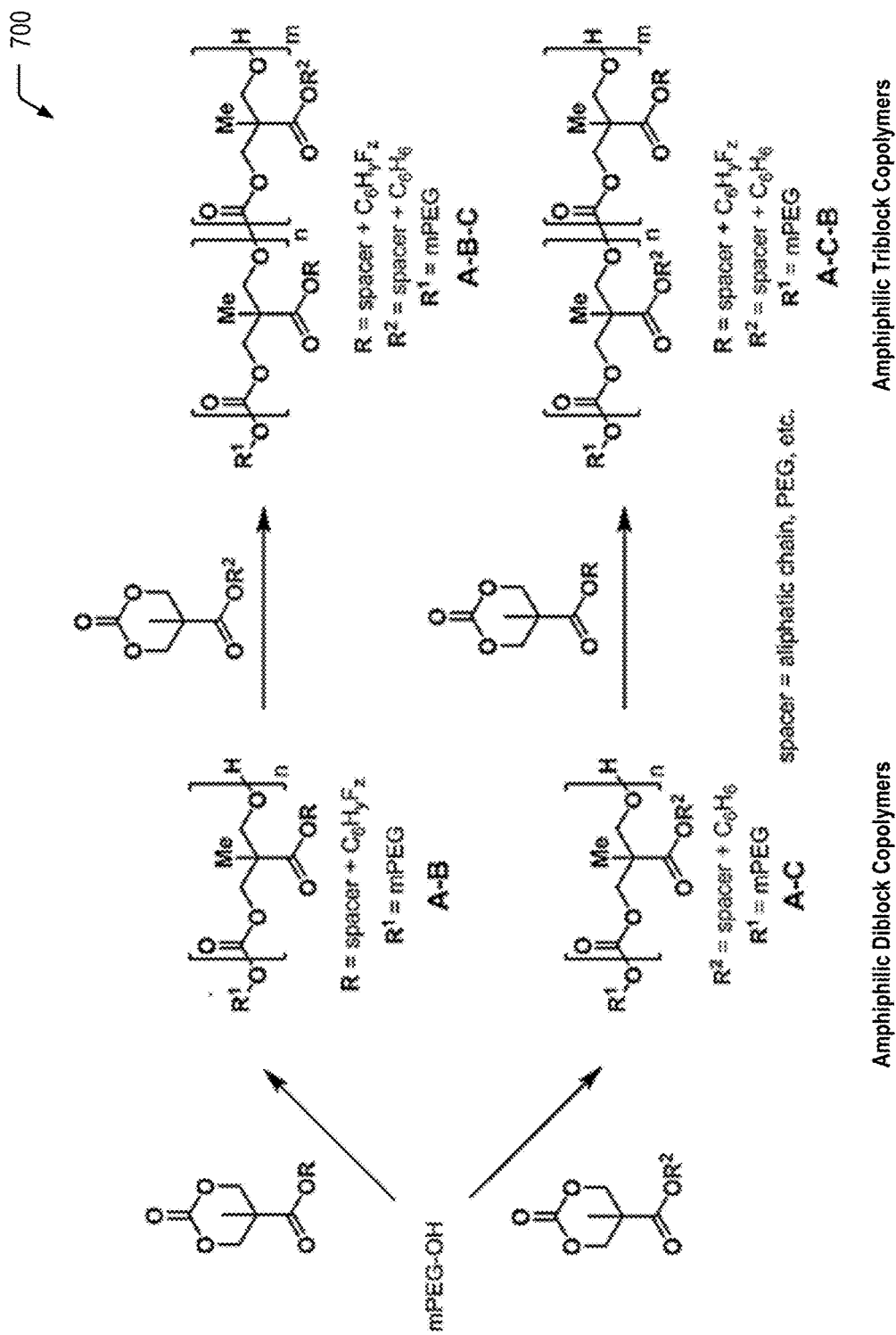
FIG. 7A is a chemical reaction diagram depicting examples of ring opening polymerization of fluorophenyl-containing carbonate monomers using monofunctional PEG initiators to yield triblock copolymers.

Referring to FIG. 7A, a chemical reaction diagram 700 depicts examples of ring opening polymerization of fluorophenyl-containing carbonate monomers (z>0) using monofunctional PEG initiators to yield triblock copolymers. In FIG. 7A, the letter A is used to designate a hydrophilic portion of the triblock copolymer, and the letters B and C are used to designate hydrophobic portions of the triblock copolymer.

In the first example depicted at the top of FIG. 7A, the ring-opening polymerization reaction includes the monofunctional PEG initiator (designated as "mPEG-OH" in FIG. 7A) and a 6-membered cyclic ring to form an amphiphilic diblock copolymer intermediate material (designated as "A-B" in FIG. 7A). As shown in FIG. 7A, the ester substituent (R) of the 6-membered cyclic ring represents a spacer and $C_6H_yF_z$, with the terminal group of the resulting intermediate material designated as R', corresponding to mPEG. The spacer may be an aliphatic chain or PEG, among other alternatives. The subsequent chemical reaction illustrates the formation of an amphiphilic triblock copolymer (designated as "A-B-C" in FIG. 7A) using the amphiphilic diblock copolymer (A-B) and another 6-membered cyclic ring having a different ester substituent ($R^2$), where $R^2$ corresponds to a spacer and $C_6H_6$. The integer n is used to designate the first hydrophobic portion (B) of the resulting amphiphilic triblock copolymer that is associated with the first 6-membered cyclic ring (with the ester substituent R). The integer m is used to designate the second hydrophobic portion (C) of the resulting amphiphilic triblock copolymer that is associated with the second 6-membered cyclic ring (with the ester substituent $R^2$).

In the second example depicted at the bottom of FIG. 7A, the ring-opening polymerization reaction includes the monofunctional PEG initiator and a 6-membered cyclic ring to form an amphiphilic diblock copolymer intermediate material (designated as "A-C" in FIG. 7A). As shown in FIG. 7A, the ester substituent ($R^2$) of the 6-membered cyclic ring represents a spacer and $C_6H_6$, with the terminal group of the resulting intermediate material designated as R', corresponding to mPEG. The spacer may be an aliphatic chain or PEG, among other alternatives. The subsequent chemical reaction illustrates the formation of an amphiphilic triblock copolymer (designated as "A-C-B" in FIG. 7A) using the amphiphilic diblock copolymer (A-C) and another 6-membered cyclic ring having a different ester substituent (R), where R corresponds to a spacer and $C_6H_yF_z$. The integer n is used to designate the first hydrophobic portion (C) of the resulting amphiphilic triblock copolymer that is associated with the first 6-membered cyclic ring (with the ester substituent $R^2$). The integer m is used to designate the second hydrophobic portion (B) of the resulting amphiphilic triblock copolymer that is associated with the second 6-membered cyclic ring (with the ester substituent R).

Figure 7B:
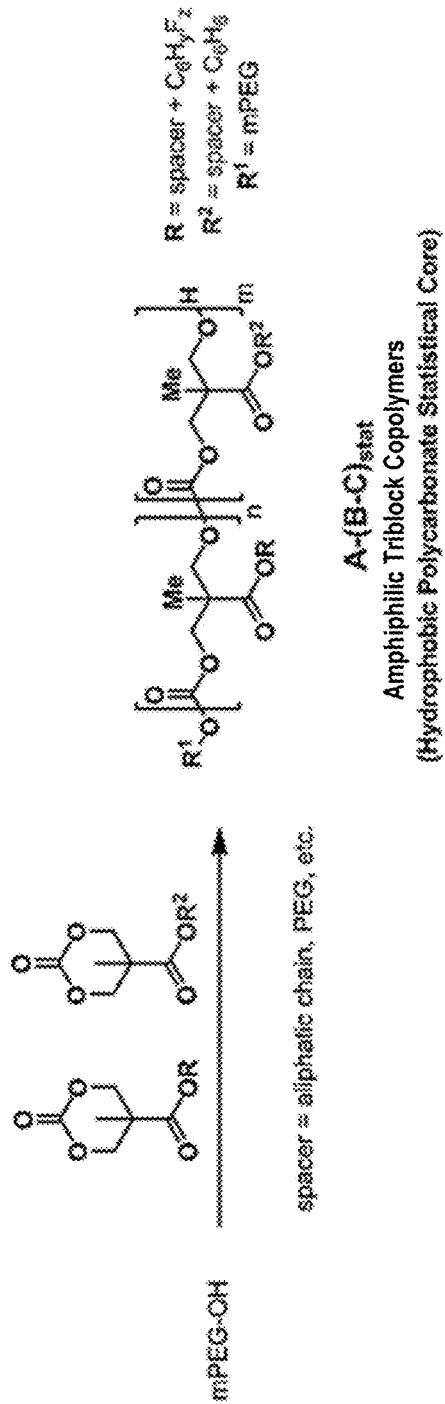
FIG. 7B is a chemical reaction diagram depicting examples of ring opening polymerization of fluorophenyl-containing carbonate monomers using a monofunctional PEG initiator to yield an amphiphilic triblock copolymer having a hydrophobic polycarbonate statistical core.

Referring to FIG. 7B, a chemical reaction diagram 800 depicts an example of ring opening polymerization of fluorophenyl-containing carbonate monomers (z>0) using a monofunctional PEG initiator to yield an amphiphilic triblock copolymer having a hydrophobic polycarbonate statistical core. The amphiphilic triblock copolymer depicted in FIG. 7B is represented as A-(B-C)$_{stat}$, with the letter A used to designate a hydrophilic portion of the triblock copolymer, and the letters B and C are used to designate hydrophobic portions of the triblock copolymer.

In the example of FIG. 7B, the ring opening polymerization reaction includes the monofunctional PEG initiator (designated as "mPEG-OH" in FIG. 7A) and two 6-membered cyclic rings having different ester substituents (designated as R and $R^2$). The two 6-membered cyclic rings depicted in FIG. 7B correspond to the example 6-membered cyclic rings depicted in the two examples of FIG. 7A. In contrast to the examples of FIG. 7A, FIG. 7B illustrates that a single ring opening polymerization reaction may be utilized to form a statistical triblock copolymer. The integer n used to represent the statistical portion of the triblock copolymer that corresponds to a first hydrophilic portion (B) associated with the first 6-membered cyclic ring (having the ester substituent R). The integer m is used to represent the statistical portion of the triblock copolymer that corresponds to a second hydrophilic portion (C) associated with the second 6-membered cyclic ring (having the ester substituent $R^2$).

Figure 8A:
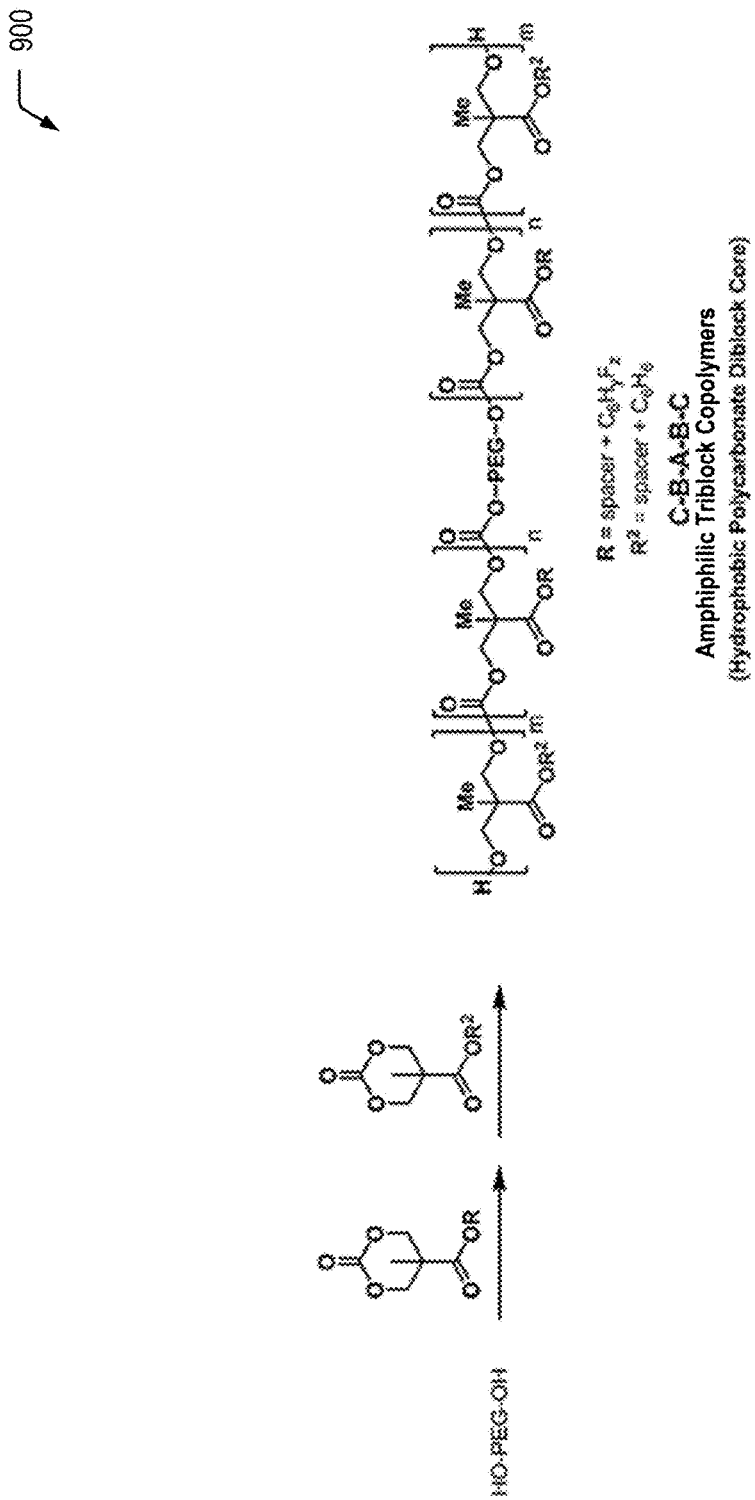
FIGS. 8A and 8B depict examples of ring opening polymerization reactions of fluorophenyl-containing carbonate monomers using different PEG initiators to yield different architectures depending on the addition order of the carbonate monomers.
Figure 8B:
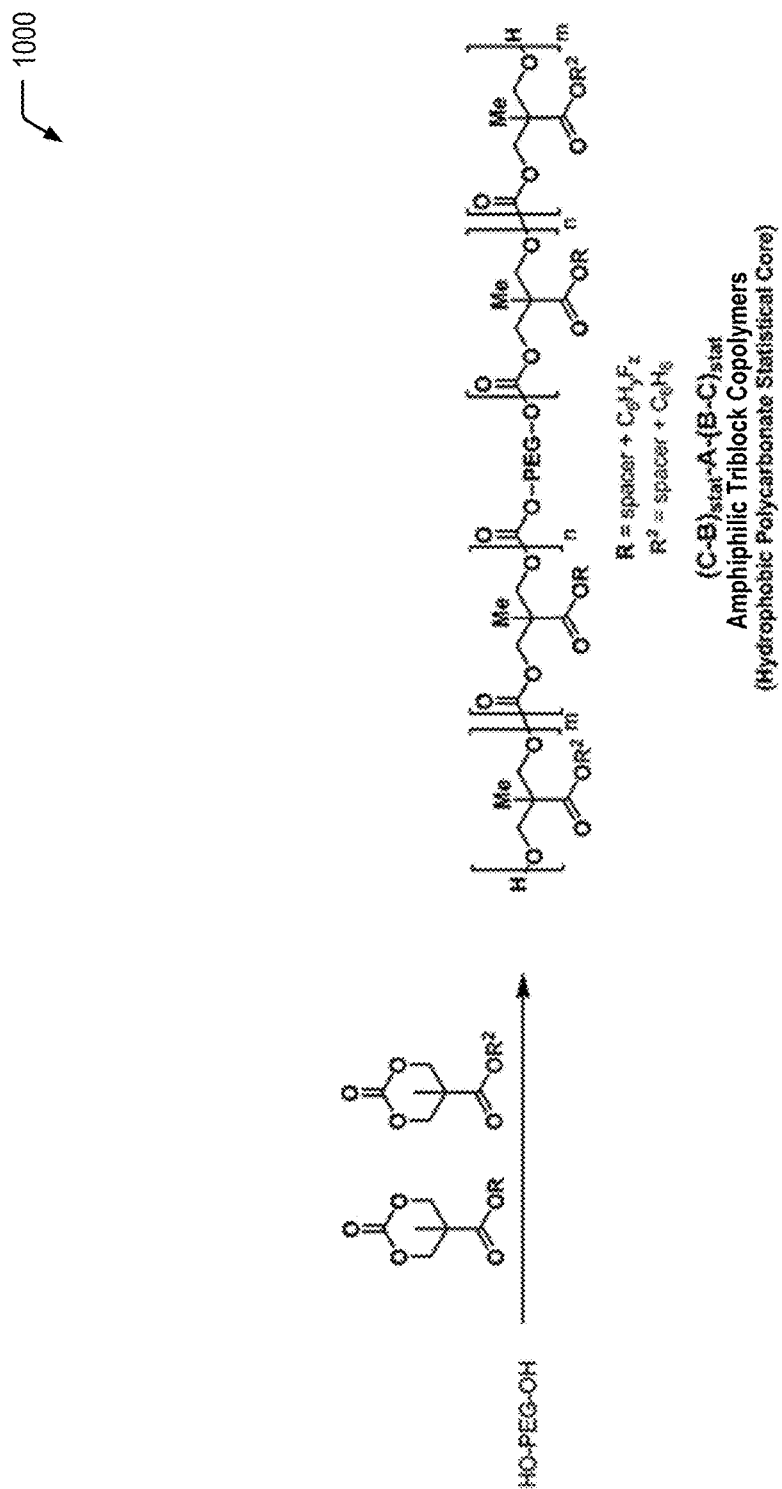

FIGS. 8A and 8B depict examples of ring opening polymerization reactions of fluorophenyl-containing carbonate monomers (z>0) using different PEG initiators to yield different architectures depending on the addition order of the carbonate monomers.

Referring to FIG. 8A, a chemical reaction diagram 900 depicts a first example of a ring opening polymerization reaction in which a difunctional PEG initiator (designated as "HO-PEG-OH" in FIG. 8A) is first reacted with a first 6-membered cyclic ring having a first ester substituent (R), followed by a reaction with a second 6-membered cyclic ring having a second ester substituent ($R^2$). The two 6-membered cyclic rings depicted in FIG. 8A correspond to the example 6-membered cyclic rings depicted in the examples of FIGS. 7A and 7B. The resulting amphiphilic triblock copolymer is designated C-B-A-B-C, with A representing the hydrophobic polycarbonate diblock core. The integer n is used to designate the hydrophobic portion (B) of the resulting amphiphilic triblock copolymer that is associated with the first 6-membered cyclic ring (with the ester substituent R). The integer m is used to designate the hydrophobic portion (C) of the resulting amphiphilic triblock copolymer that is associated with the second 6-membered cyclic ring (with the ester substituent $R^2$).

As shown in the example of FIG. 8A, the B groups adjacent to the PEG core are associated with the first 6-membered cyclic ring having the first ester substituent (R) that are joined to the PEG core in the first chemical reaction. The C groups adjacent to the B groups are associated with the second 6-membered cyclic ring having the second ester substituent ($R^2$) that are joined to the B groups in the second chemical reaction. In other cases, the difunctional PEG initiator may first be reacted with the 6-membered cyclic ring having the second ester substituent ($R^2$), followed by a reaction with the 6-membered cyclic ring having the first ester substituent (R). Thus, while not shown in the example of FIG. 8A, a different addition order may result in an amphiphilic triblock copolymer with a sequence B-C-A-C-B.

Referring to FIG. 8B, a chemical reaction diagram 1000 depicts an example of ring opening polymerization of fluorophenyl-containing carbonate monomers (z>0) using a monofunctional PEG initiator to yield an amphiphilic triblock copolymer having a hydrophobic polycarbonate statistical core. The amphiphilic triblock copolymer depicted in FIG. 8B is represented as (C-B)$_{stat}$-A-(B-C)$_{stat}$, with the letter A used to designate the PEG core, and the letters B and C are used to designate hydrophobic portions of the triblock copolymer associated with different 6-membered cyclic rings having different ester substituents (designated as R and $R^2$)

The two 6-membered cyclic rings depicted in FIG. 8B correspond to the example 6-membered cyclic rings depicted in FIG. 8A. In contrast to FIG. 8A, FIG. 8B illustrates that a single ring opening polymerization reaction may be utilized to form a statistical triblock copolymer. The integer n used to represent the statistical portion of the triblock copolymer that corresponds to a first hydrophilic portion (B) associated with the first 6-membered cyclic ring (having the ester substituent R). The integer m is used to represent the statistical portion of the triblock copolymer that corresponds to a second hydrophilic portion (C) associated with the second 6-membered cyclic ring (having the ester substituent $R^2$).

Stable non-objects utilizing the arene-fluoroarene interactions can be obtained from A-B/A-C mixtures or A-B-C, A-C-B, A-(B-C)$_{stat}$ triblock copolymers (see FIGS. 7A and 7B). As previously described herein, the slipped (or parallel-displaced) and T-shaped configurations are favored for arene-arene interactions, while the slipped and face-to-face configurations are favored for arene-perfluoroarene interactions. Therefore, the geometrical conformation of the arene-fluoroarene interactions may yield self-assembled structures that are not observed with regular arene-arene pi-pi stacking (e.g., elongated micelles, compartment micelles, fibers, etc.). The formation of such nano-assemblies may also be driven by changing the copolymer/copolymer mixture compositions.

The formation of physical hydrogels is typically observed when using A-B-A triblock copolymers that can form flower-like micelles. In most cases, A is a hydrophobic block exhibiting inter-chain physical interactions (e.g., hydrophobic interactions, pi-pi stacking, etc.), and B is a hydrophilic block (although hydrogels using B-A-B copolymers may be used). To make those hydrogels more stable, several strategies may be used. One example strategy is chemical cross-linking of the hydrophobic cores of the flower-like micelles post-gelation. Another example strategy is reinforcement of the physical inter-chain interactions of the A blocks. While the first strategy offers the possibility of synthesizing strong gels, the gels may not exhibit the shear-thinning properties that most physical gels exhibit. One way to reinforce the interactions is to introduce fluoroarene moieties to allow for stronger pi-pi stacking interactions. Therefore, C-B-A-B-C, B-C-A-C-B, and $(C-B)_{stat}$-A-$(B-C)_{stat}$, as depicted in FIGS. 8A and 8B, may be more likely to form shear-thinning physical hydrogels that are stronger than if a C-A-C material were to be used.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. An amphiphilic block copolymer comprising:

a poly(ethylene glycol) (PEG) block;

a first hydrophobic polycarbonate (PC) block bonded to the PEG block, the first hydrophobic PC block including pendant fluoroaryl substituents;

a second hydrophobic PC block bonded to the first hydrophobic PC block, the second hydrophobic PC block including pendant aryl substituents;

a third hydrophobic PC block bonded to the PEG block, the third hydrophobic PC block including the pendant fluoroaryl substituents; and a fourth hydrophobic PC block bonded to the third hydrophobic PC block, the fourth hydrophobic PC block including the pendant aryl substituents.

2. An amphiphilic block copolymer comprising:

a poly(ethylene glycol) (PEG) block;

a first hydrophobic polycarbonate (PC) block bonded to the PEG block, the first hydrophobic PC block including pendant aryl substituents;

a second hydrophobic PC block bonded to the first hydrophobic PC block, the second hydrophobic PC block including pendant fluoroaryl substituents;

a third hydrophobic PC block bonded to the PEG block, the third hydrophobic PC block including the pendant aryl substituents; and a fourth hydrophobic PC block bonded to the third hydrophobic PC block, the fourth hydrophobic PC block including the pendant fluoroaryl substituents.

* * * * *